(12) United States Patent
Burnett

(10) Patent No.: US 7,335,179 B2
(45) Date of Patent: Feb. 26, 2008

(54) VESICULAR SHUNT FOR THE DRAINAGE OF EXCESS FLUID

(75) Inventor: Daniel Rogers Burnett, Menlo Park, CA (US)

(73) Assignee: Novashunt AG, Steinhausen (CH)

( * ) Notice: Subject to any disclaimer, the term of this patent is extended or adjusted under 35 U.S.C. 154(b) by 553 days.

(21) Appl. No.: 10/369,550

(22) Filed: Feb. 21, 2003

(65) Prior Publication Data

US 2003/0163079 A1    Aug. 28, 2003

Related U.S. Application Data

(60) Provisional application No. 60/389,346, filed on Jun. 18, 2002, provisional application No. 60/359,287, filed on Feb. 25, 2002.

(51) Int. Cl.
*A61M 5/00* (2006.01)

(52) U.S. Cl. .......................................... 604/9

(58) Field of Classification Search ............. 604/7–10, 604/890.1, 891.1, 93.01, 94.01, 96.01, 104, 604/544, 245–247, 264, 523, 540; 623/3.1, 623/3.26, 3.28, 11.11, 23.64, 66.1; 128/898
See application file for complete search history.

(56) References Cited

U.S. PATENT DOCUMENTS

| | | | |
|---|---|---|---|
| 3,654,932 A * | 4/1972 | Newkirk et al. ............... 604/9 |
| 4,083,786 A | 4/1978 | Tsuda et al. |
| 4,261,341 A * | 4/1981 | Hakim et al. .................. 604/9 |
| 4,610,658 A * | 9/1986 | Buchwald et al. ............. 604/9 |
| 4,963,129 A | 10/1990 | Rusch |
| 5,078,688 A | 1/1992 | Lobodzinski et al. |
| 5,395,350 A | 3/1995 | Summers |
| 5,725,506 A | 3/1998 | Freeman et al. |
| 5,830,172 A | 11/1998 | Leveen et al. |
| D420,738 S | 2/2000 | Carter et al. |
| 6,689,085 B1 * | 2/2004 | Rubenstein et al. ........... 604/9 |

OTHER PUBLICATIONS

Rozenblit, Grigory N, Peritoneal-Urinary Drainage for Treatment of Refractory Ascites: A Pilot Study, Journal of Vascular & Interventional Radiology, Nov./Dec. 1998, 9(6):998-1005, NY.

* cited by examiner

*Primary Examiner*—Patricia Bianco
(74) *Attorney, Agent, or Firm*—Franco A. Serafini; Luce, Forward, Hamilton & Scripps LLP

(57) ABSTRACT

A transvesicular drainage device, designed to drain excess fluid from a variety of locations in the human body into the bladder. The device may be used to treat ascites or any fluid collection within the body of a human, or a non human mammal.

41 Claims, 8 Drawing Sheets

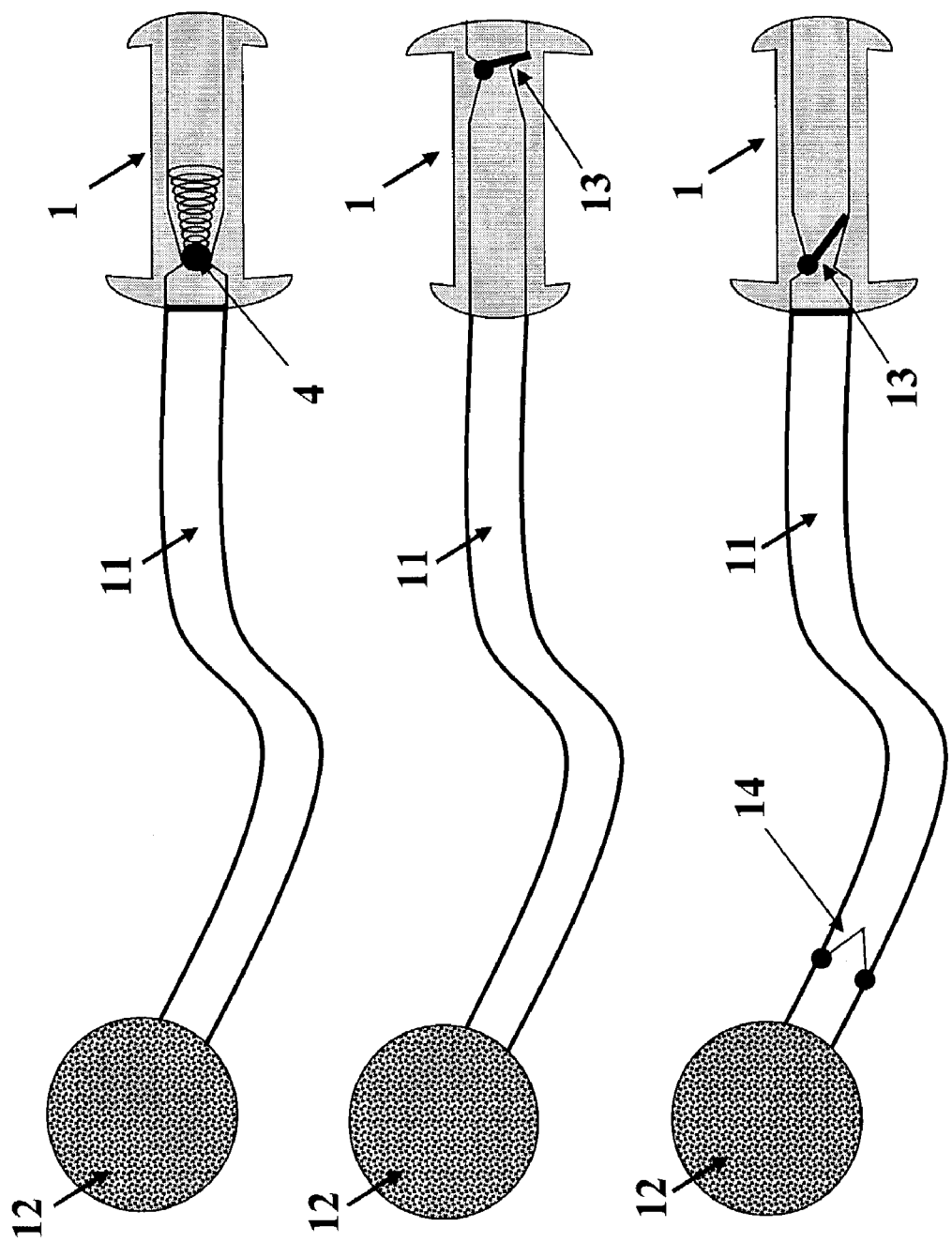

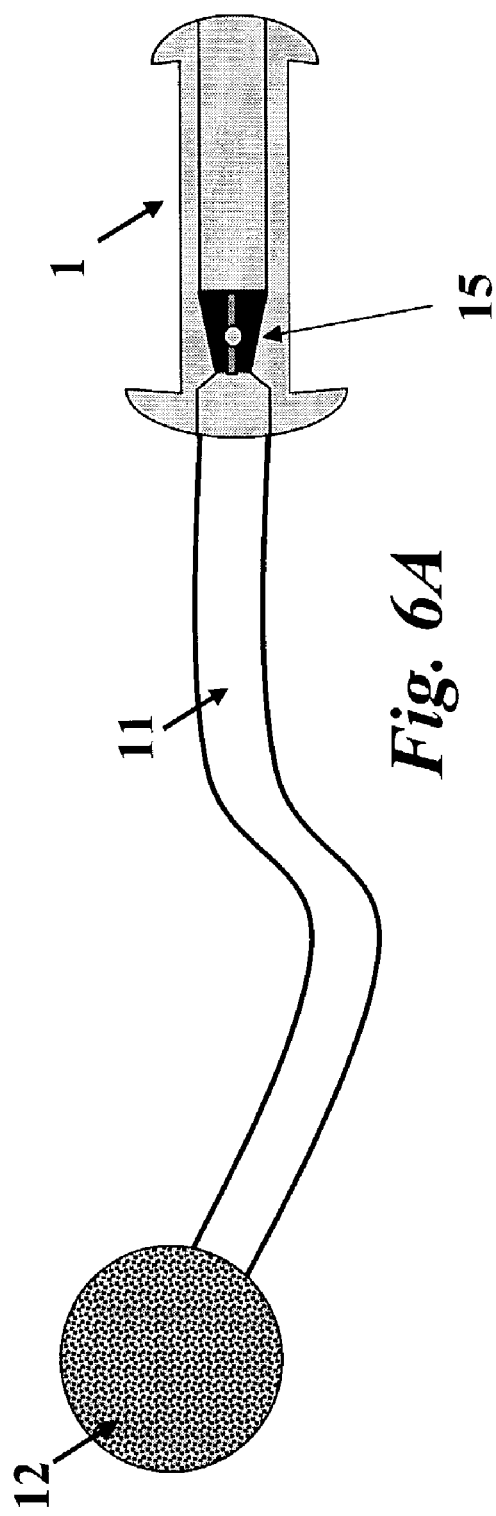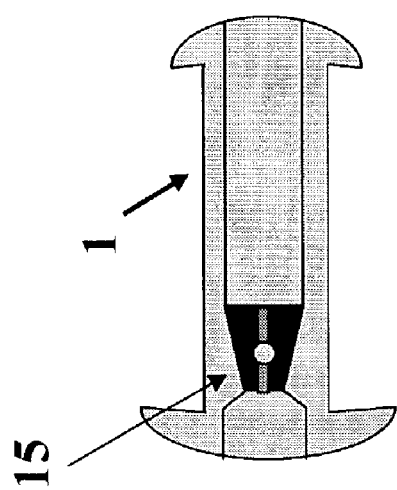
Fig. 6A
Fig. 6B

VESICULAR SHUNT FOR THE DRAINAGE OF EXCESS FLUID

CROSS-REFERENCE TO RELATED APPLICATIONS

This application claims the priority of U.S. Provisional Application Ser. No. 60/359,287, filed on Feb. 25, 2002 and U.S. Provisional Application Ser. No. 60/389,346 filed on Jun. 18, 2002. The aforementioned provisional applications are incorporated by reference herein for all purposes.

FIELD OF THE INVENTION

The invention is a transvesicluar drainage device designed to drain excessive fluid from a bodily cavity into the bladder.

BACKGROUND OF THE INVENTION

The present invention pertains to a chronic excess fluid drainage device. More specifically, the present invention pertains to a vesicular drainage device permitting unidirectional flow of excess fluid collections into the bladder.

In medicine there are a variety of conditions which result in pathologic chronic collection of bodily fluids. Chronic pericardial effusions, normopressure hydrocephalus, hydrocephalus, chronic pulmonary effusion, and ascites are but a few of the conditions in which chronic fluid collections persist and result in increased morbidity and mortality.

These conditions currently are treated by one of two methods: 1) external drainage with a high-risk of infection and long-term requirement for multiple punctures, 2) drainage to another body-cavity, or 3) various drugs. For pericardial effusions and hydrocephalus of all types, the treatment of choice is drainage to another region of the body. For pericardial effusions this entails a pericardial window, a highly invasive procedure in which a large section of the external heart cavity is removed. For hydrocephalus, the treatment typically involves the use of a ventriculo-peritoneal shunt draining the cerebrospinal fluid into the peritoneal cavity. This device frequently becomes clogged due to the proteinaceous environment of the peritoneal cavity and requires removal or revision.

One conception of the present invention pertains to an ascites drainage device. More specifically, said conception pertains to a peritoneovesicular drainage device permitting unidirectional flow of peritoneal fluid from the peritoneal cavity into the bladder.

Ascites is a highly debilitating complication associated with many medical conditions including liver failure and congestive heart failure. Untreated ascites can result in respiratory compromise, compression of the inferior vena cava (a vital blood vessel) and spontaneous bacterial peritonitis (a life-threatening condition). In order to treat chronic ascites, medicine has turned to both drugs and surgery.

The drugs required to treat ascites are typically long-term and frequently result in complications. The most common pharmaceutical treatment of ascites involves the use of diuretics to remove fluid from patient's body through their urine. The difficulty with this treatment, though, is that fluid is removed from the entire body, including the circulating volume of blood, and can result in excessive loss of fluid required to perfuse the vital organs of the human body. Thus, even with religious application, though, the medicines frequently fail. In this case, surgical, or invasive, procedures are indicated.

Currently the treatment of choice is called paracentesis. In paracentesis, the peritoneal fluid is drained through the abdominal wall via the insertion of a needle through the abdominal wall into the peritoneal cavity. This procedure, though, is only a temporary fix as the ascites quickly refills the peritoneal cavity in most chronic conditions. Furthermore, repeated paracenteses put the patient at increased risk for a life-threatening infection of their peritoneal cavity. Other surgical/invasive procedures involve treatment of the cause of the ascites (for example the Transjugular Intrahepatic Portosystemic Shunt) but these measures also frequently result in complications, which are often serious, and are thus performed hesitantly.

The present invention avoids the difficulties associated with the current therapies for chronic ascites, namely, the procedure allows the drainage of peritoneal fluid without 1) the serious complications of pharmaceuticals, 2) the inconvenience, the substantial costs and the increased risk of infection associated with frequent paracenteses and 3) the multiple severe complications associated with more invasive and risky surgical operations to treat the cause of ascites.

None of the existing devices are able to drain the peritoneal cavity except through temporary transabdominal insertion of a drainage catheter. These devices provide little improvement over the intermittent punctures of paracentesis and result in increased rates of infection if left in place for any length of time. The present invention will obviate the need for a long-term abdominal incision and, therefore, will eliminate the associated increased risk of serious infection.

SUMMARY OF THE INVENTION

The present invention is a device designed for implantation in the wall of the bladder that permits the drainage of excessive fluid into the bladder.

The device consists of a hollow, cylindrical column with flanges at both ends to provide secure anchorage in the bladder wall. Preferably there is a mechanism to provide unidirectional flow of fluid and prevent reflux of urine inside the column. A preferred embodiment of the device provides a passive ball-valve mechanism which allows for drainage of fluid into the bladder whenever a certain pressure is achieved at the collection site. A second preferred embodiment of the device provides an active valve mechanism which allows for controlled drainage of fluid into the bladder whenever the valve is actuated. The most preferred embodiment provides a pump in addition to an active valve mechanism.

For ascites, the device can be implanted either through a transurethral or transabdominal route. In order to drain other sites, the bladder component is implanted as above, and a flexible tube or other conduit may be incorporated to place the receptacle end of the device in a fashion tailored to the region to be drained.

In all embodiments, it is preferred that the device is constructed with biocompatible materials.

BRIEF DESCRIPTION OF THE DRAWINGS

FIG. 5 is an illustration of alternative embodiments of the invention with differing valve types, differing valve positioning and differing number of valves.

FIG. 6 is an illustration of an alternative embodiment of the device in which an active, externally or internally controlled valve is utilized.

DESCRIPTION OF THE PREFERRED EMBODIMENTS

Figure 1:
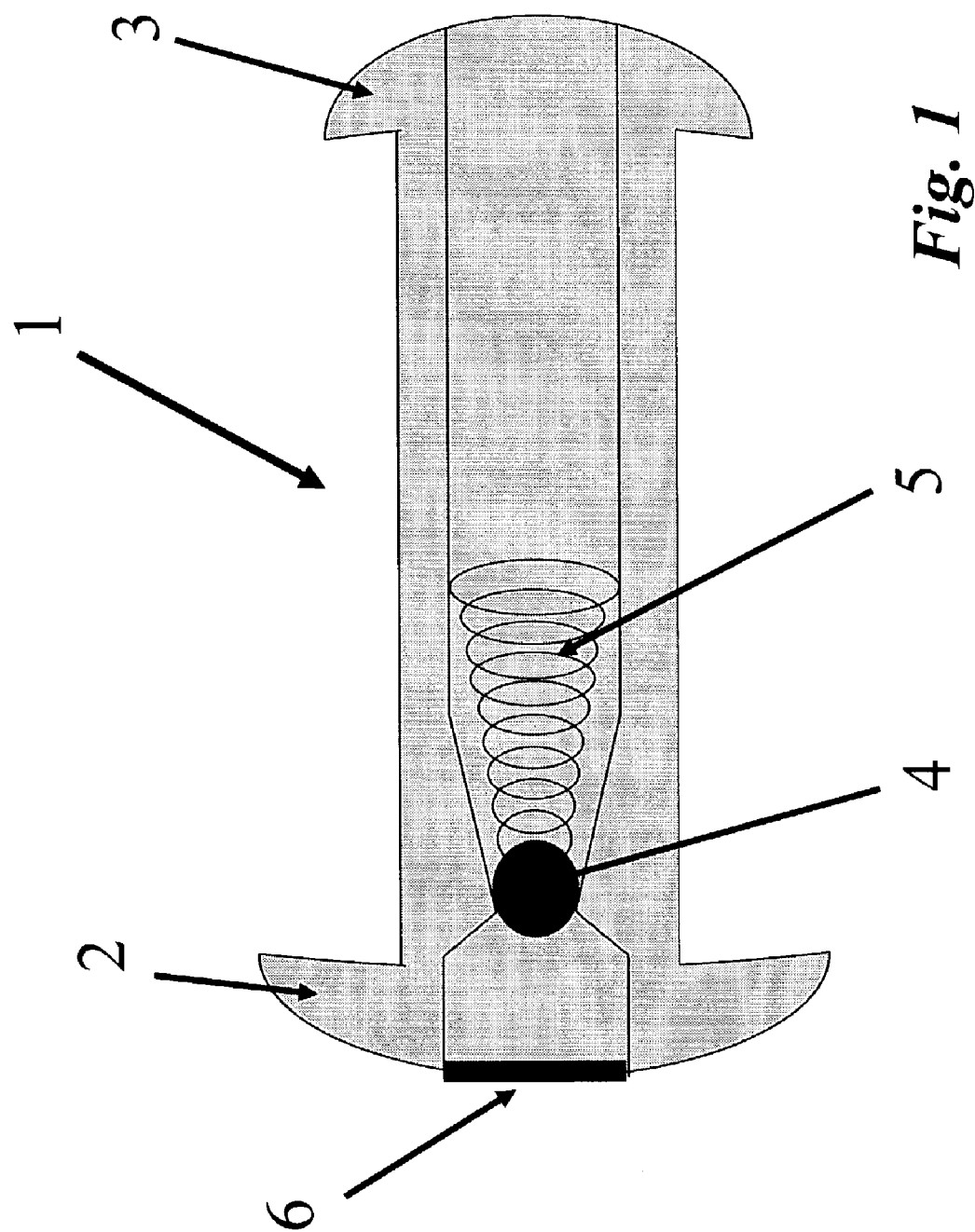
FIG. 1 shows a cross-sectional view of the device.

As can be seen in FIG. 1, the present invention provides a novel vesicular drain 1 for implantation in the bladder wall 9 which will provide for unidirectional drainage of fluid into the bladder. The drain 1 provides two flanges at its ends 2, 3 which allow the device to be firmly anchored once placed across the bladder wall 9. Alternative embodiments of the device may use other anchoring mechanisms, including, but not limited to: a screw thread on the outside of 1, staples, sutures, an adhesive compound, and/or one or more barbs.

The hollow shaft of the device contains a ball-valve 4 through which a positive closing pressure is provided by an attached spring 5.

The fluid collection interface of the device 1 may optionally include a large pore mesh 6 to allow for free flow of fluid while preventing incarceration of tissues at the drainage site.

Figure 2:
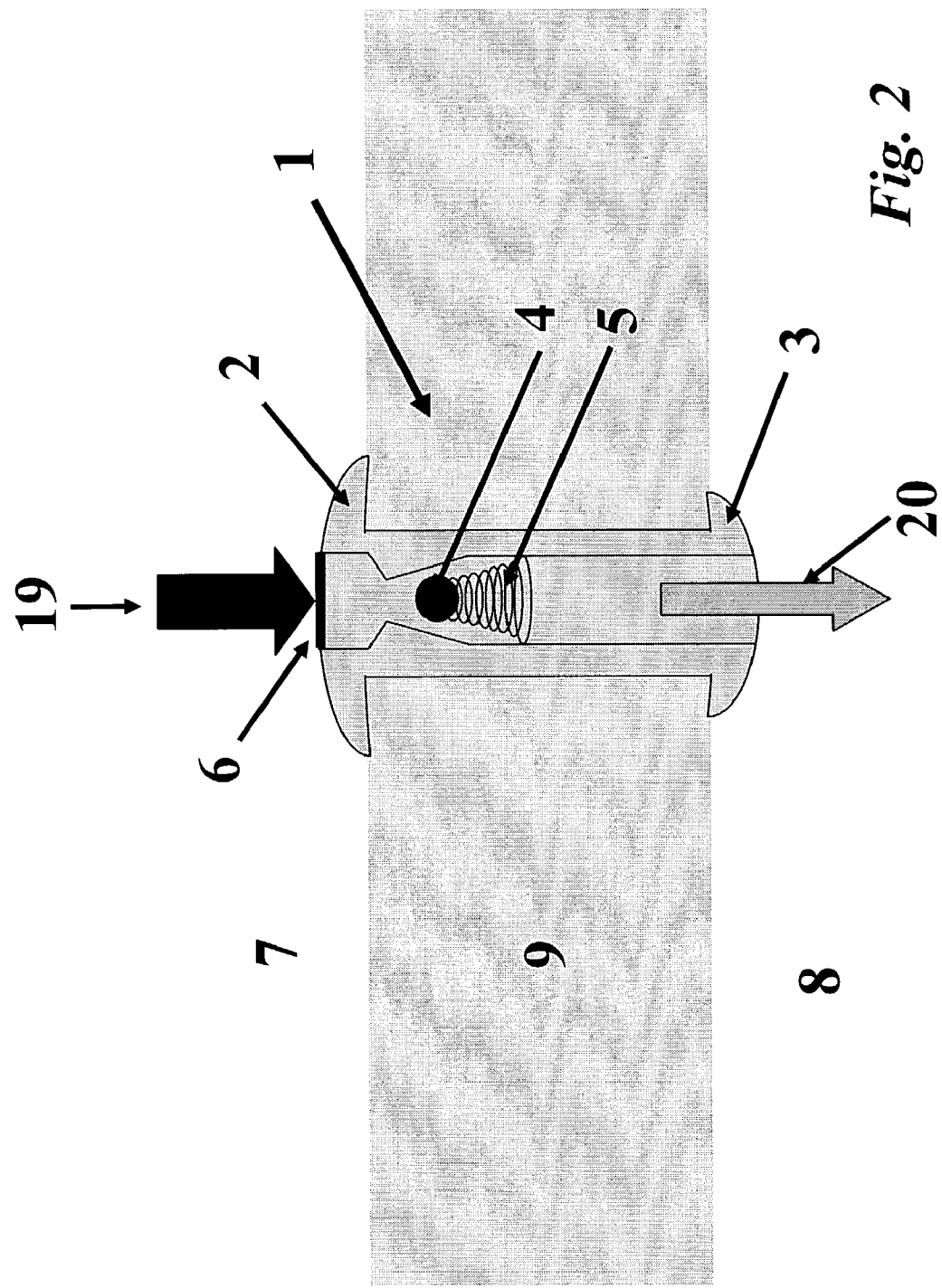
FIG. 2 shows a cross-sectional view of the implanted device, designed to treat ascites, when the peritoneal pressure is sufficient to permit drainage.

As can be seen in FIG. 2, once the pressure of the fluid collection (in this case the peritoneal cavity) 7 exceeds the combined force of the spring 5 and the pressure of the fluid-filled bladder cavity 8, the peritoneal fluid 19 flows into the bladder cavity 8 through displacement of the ball-valve 4. There, the peritoneal fluid mixes with the urine 20.

Figure 3:
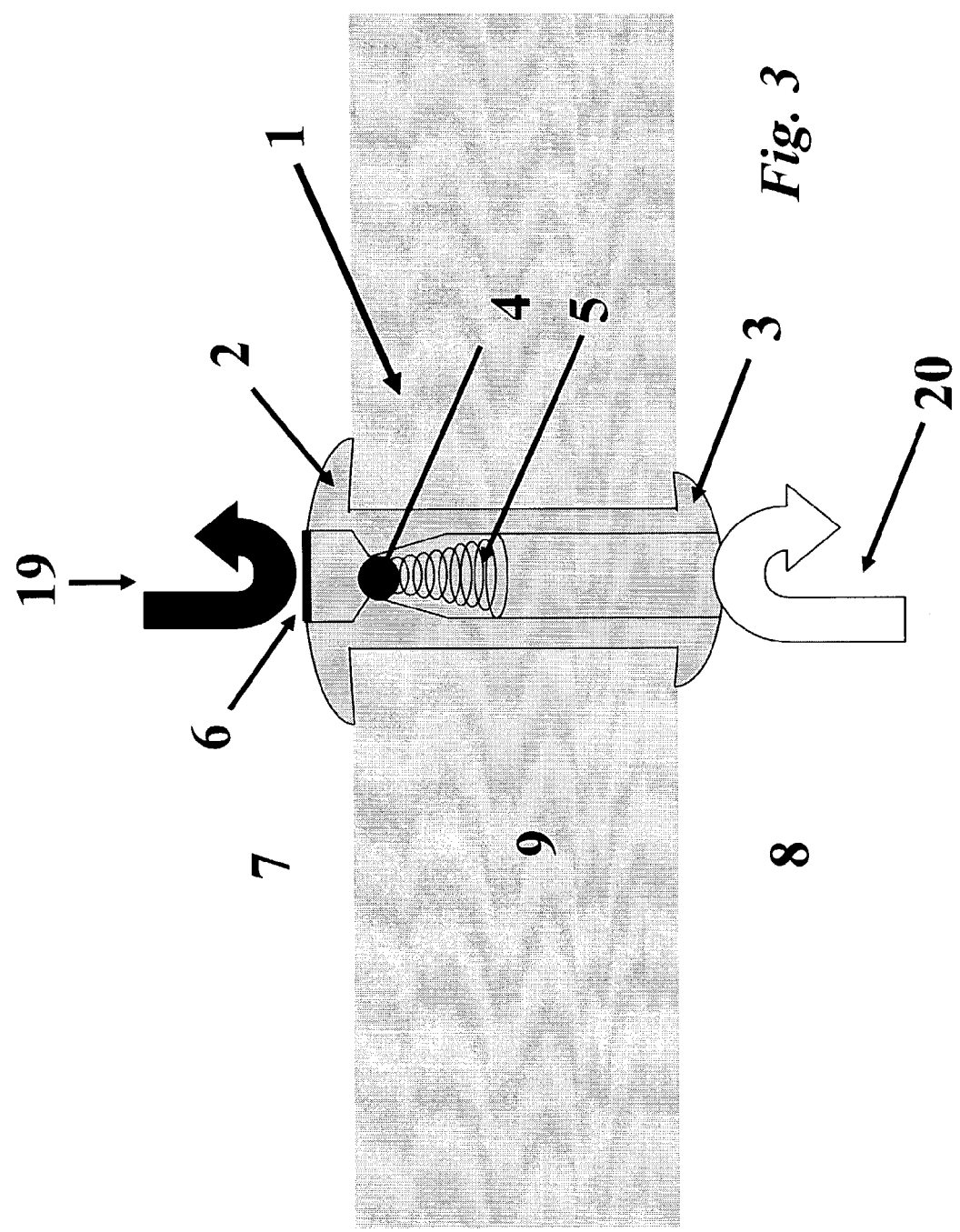
FIG. 3 shows a cross-sectional view of the implanted device, designed to treat ascites, when the peritoneal pressure is not sufficient to open the valve and no fluid flow occurs.

If the pressure of the bladder cavity 8 and the force of the spring 5, though, are greater than the pressure of the fluid collection (in this case the peritoneal cavity) 7, then the valve 4 will remain closed preventing reflux of urine 19 into the peritoneal cavity as depicted in FIG. 3.

Figure 4:
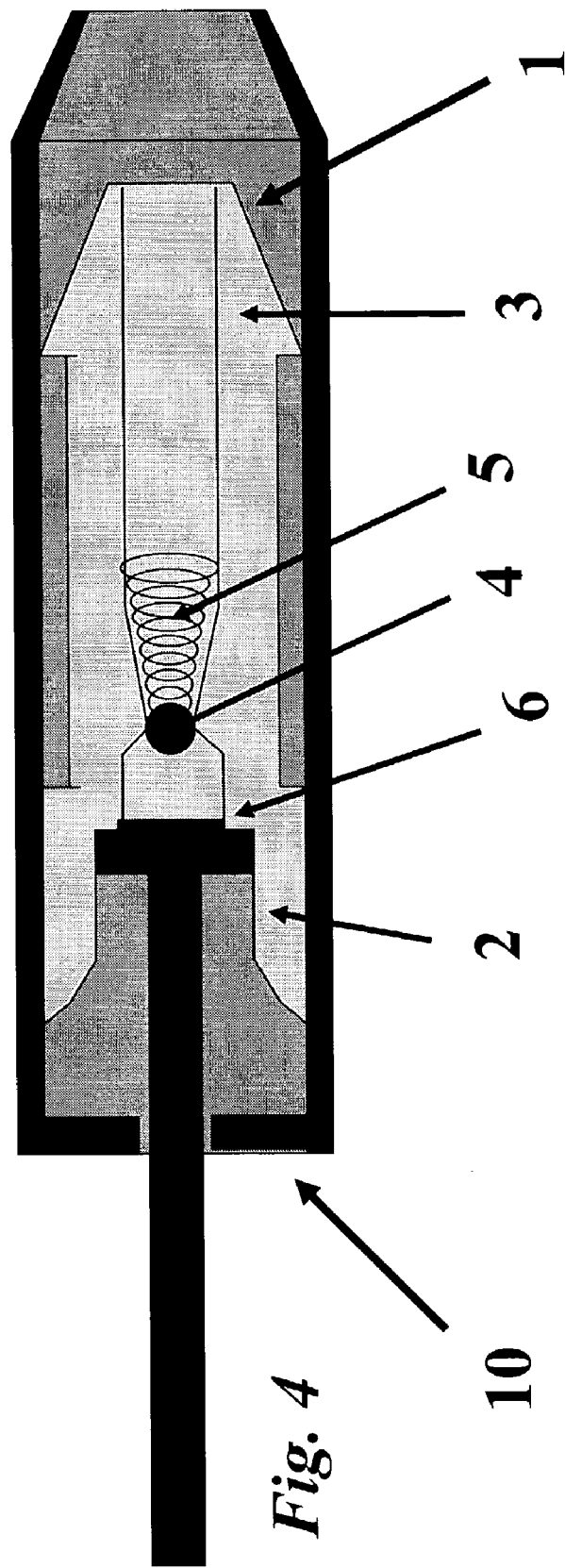
FIG. 4 is an illustration of an example of an insertion device through which the current invention can be implanted in the bladder wall.

The device is designed to be placed transurethrally or transabdominally via an insertion device 10 such as that depicted in FIG. 4. The method of insertion allows for a single invasive procedure to provide a long-term solution to the otherwise difficult problem of refractory, chronic ascites.

Alternatively, the device may contain a length of tubing 11 or other means of fluid transport to reach the fluid collection as well as an optional perforated receptacle 12, 17 and 18 through which the fluid collection will drain into the tubing. Such other means of fluid transport include, but are not limited to, conduit, catheter, channel, lumen, hose, pipe, duct, artery or vessel. The device may contain one or more valves of a variety of types including passive valves 4, 13 (flapper-valve), 14 (in FIG. 5), or active valves 15 (in FIG. 6) for tighter control of fluid drainage.

Figure 7:
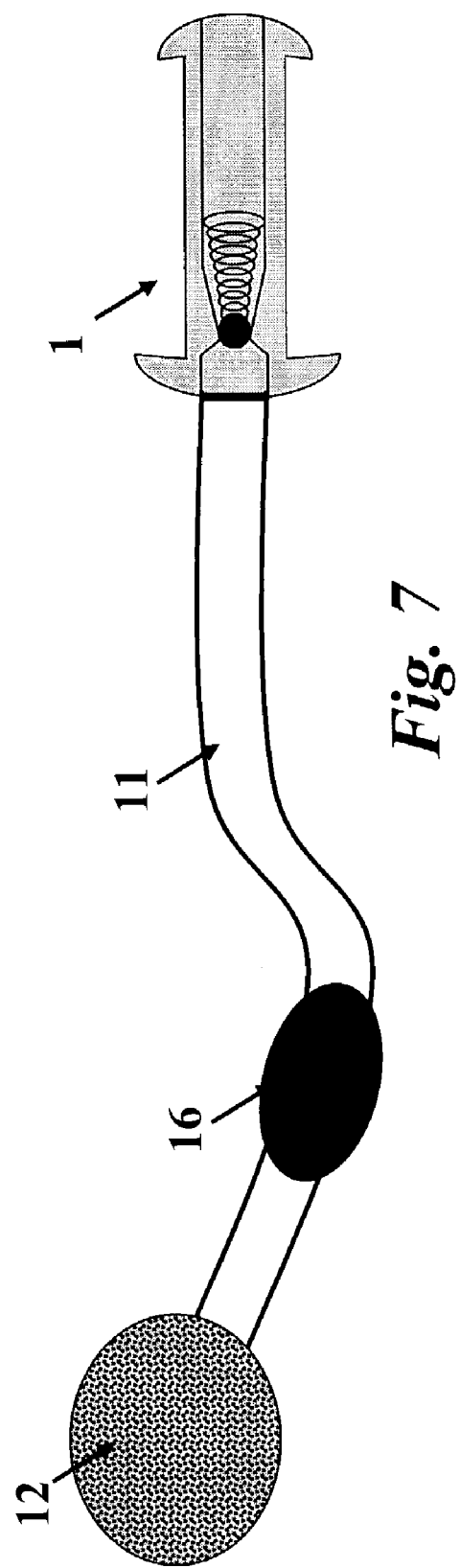
FIG. 7 is an illustration of an alternative embodiment of the device in which a pump is included along the length of the tubing and placed subcutaneously for external control of drainage with a passive valve.

The device is also designed to be able to incorporate a pump mechanism 16 in FIG. 7 which, when placed subcutaneously, can be actuated to provide an active pumping mechanism with the passive valves 4, 13, 14, or with an active valve 15. A third embodiment of the invention involves a unidirectional pump in place of the valve, controlling the flow of fluid through the device. A fourth conception of the invention involves a single unidirectional valve controlling the flow of fluid through the device.

Alternatively, maneuvers which increase the pressure of the fluid cavity can also be utilized with the passive valves 4, 13, 14 to affect drainage such as bearing down to increase intraabdominal pressure to drain the peritoneal cavity or application of a girdle designed to increase abdominal pressure.

Figure 8A:
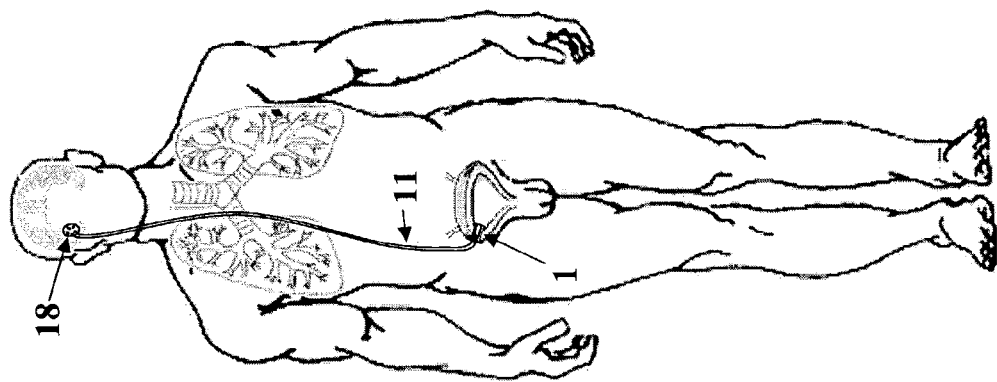
FIG. 8 is an illustration of a few of the alternative embodiment of the device in which the peritoneal cavity, the pulmonary space and the ventricular space are able to be drained (pericardial drainage device not shown).
Figure 8B:
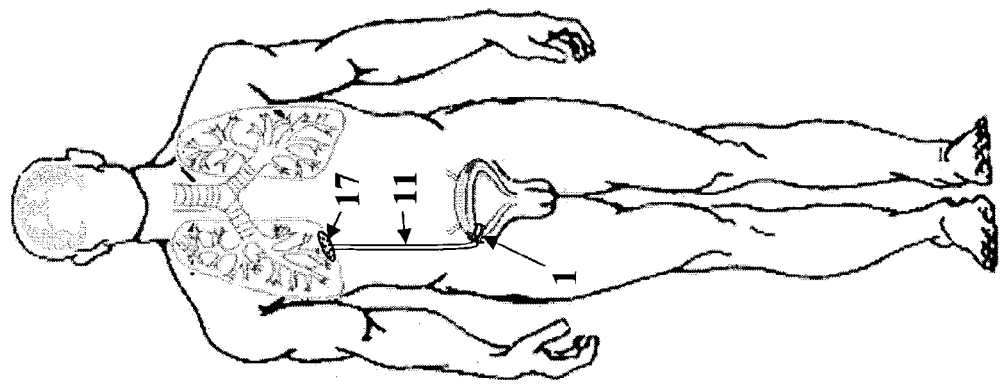
Figure 8C:
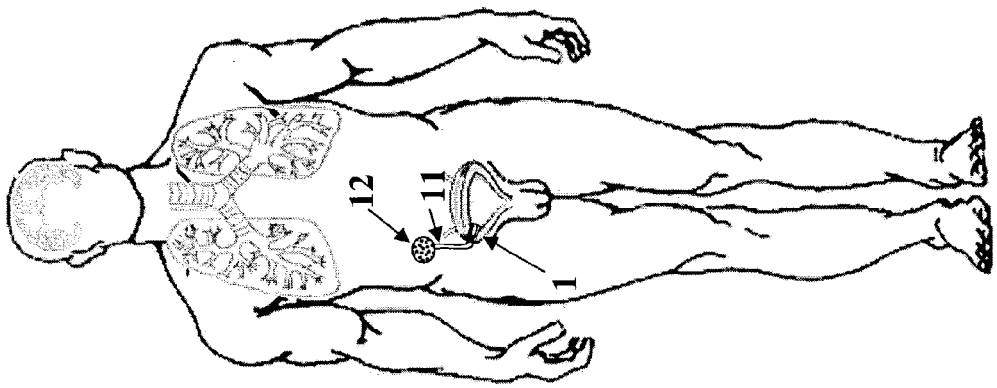

The device will be designed to drain a variety of different fluid collections including, but not limited to, the peritoneal cavity FIG. 8A, pulmonary effusions FIG. 8B and excessive cerebrospinal fluid FIG. 8C. Pericardial effusion drain is not shown.

Of particular interest to the inventors is the use of the invention to drain pulmonary effusions and other fluid collections in the lungs, in FIG. 8B.

While these are the preferred embodiments, the device could employ any mechanism which provides a unidirectional passive or active valve for the drainage of any body fluid into the urinary bladder. This could involve filtration of the fluid through a polymer so as to sequester albumin and other proteins in the fluid collection while allowing flow of water and ions across the semi-permeable membrane. This could also involve an electronic valve triggered via communication across the tissues of the human body through EMFs such as radio, electricity, pressure, mechanical, magnetism, or other means of communication, allowing drainage only at selected times. The valve of the device can take many shapes and the device can be manufactured from any of a variety of materials with the only requirement being that of biocompatibility. Alternatively, the device, in either the active or passive embodiment, may incorporate anti-infective components in order to prevent the spread of infection between the body cavities. Such anti-infective components include, but are not limited to, bacteriostatic materials, bacteriocidal materials, one or more antibiotic dispensers, antibiotic eluting materials, entrained radioisotopes, a heating element, bioactive plastics, surfaces which encourage epithelialization, and coatings which prevent bacterial adhesion. Alternatively, the device, in either the active or passive embodiment, may incorporate anti-clogging components. Such anti-clogging components include, but are not limited to, an active ultrasonic component, an inner and outer sleeve which, when actively agitated, disrupt the inner lumen, surfaces which encourage epithelialization, enzyme eluting materials, enzyme eluting materials which specifically target the proteinaceous components of ascites, chemical eluting surfaces, an intermittent plunger mechanism, and coatings which prevent adhesion of proteinaceous compounds.

While the device is primarily contemplated for use in human patients, the inventors also contemplate that the invention will have veterinary uses or product development purposes in equine, bovine, canine, feline, and other mammalian species.

The invention claimed is:

1. A vesicular shunt, comprising:
   a hollow cylinder, having an inside and an outside, and also having an inflow end and an outflow end;
   a valve, located inside said hollow cylinder, wherein said valve regulates the flow of fluid within the hollow cylinder such that fluid may flow from the inflow end of said hollow cylinder to the outflow end of said hollow cylinder;

wherein said valve is an active-valve controlled through an electric signal; and a flexible tube, having an inflow and an outflow end, the outflow end of said flexible tube being in fluid communication with the inflow end of said hollow cylinder.

2. A vesicular shunt as recited in claim 1, further comprising:
- a first flange, located on the outside of said hollow cylinder near the first end; and
- a second flange, located on the outside of said hollow cylinder near the second end.

3. A vesicular shunt, comprising:
- a hollow cylinder, having an inside and an outside, and also having an inflow end and an outflow end;
- a valve, located inside said hollow cylinder, wherein said valve regulates the flow of fluid within the hollow cylinder such that fluid may flow from the inflow end of said hollow cylinder to the outflow end of said hollow cylinder;
- wherein said valve is an active-valve controlled through an EMF signal; and
- a flexible tube, having an inflow and an outflow end, the outflow end of said flexible tube being in fluid communication with the inflow end of said hollow cylinder.

4. A vesicular shunt as recited in claim 3, wherein said EMF signal is a radio signal.

5. A vesicular shunt as recited in claim 1, further comprising a mesh attached to the inflow end of said hollow cylinder.

6. A vesicular shunt as recited in claim 1, further comprising a perforated receptacle attached to the inflow end of said flexible tube.

7. A vesicular shunt as recited in claim 1, further comprising a valve located within the flexible tube near the inflow end of said flexible tube.

8. A vesicular shunt as recited in claim 1, further comprising a pump, attached to the flexible tube so that said pump is capable of moving fluid from the inflow end of said flexible tube to the outflow end.

9. A vesicular shunt for draining bodily fluids, comprising:
- a tube, wherein said tube is designed to be implanted in the wall of the bladder;
- a means for preventing the passage of solids through said tube;
- a means for anchoring said tube in the wall of the bladder; and
- a means for ensuring unidirectional flow through said tube.

10. A vesicular shunt as recited in claim 9, wherein said means for anchoring is a pair of flanges.

11. A vesicular shunt as recited in claim 9, wherein said means for anchoring is a suture.

12. A vesicular shunt as recited in claim 9, wherein said means for ensuring unidirectional flow is a valve.

13. A vesicular shunt as recited in claim 12, wherein said valve is a ball-valve.

14. A vesicular shunt as recited in claim 12, wherein said valve is a flapper-valve.

15. A vesicular shunt as recited in claim 12, wherein said valve is an active-valve.

16. A vesicular shunt as recited in claim 15, wherein said active-valve is controlled through an EMF signal.

17. A vesicular shunt as recited in claim 16, wherein said EMF signal is a radio signal.

18. A vesicular shunt as recited in claim 15, wherein said active-valve is controlled through an electric signal.

19. A vesicular shunt as recited in claim 15, wherein said active-valve is controlled through a pressure signal.

20. A vesicular shunt as recited in claim 15, wherein said active-valve is controlled through a mechanical signal.

21. A vesicular shunt as recited in claim 15, wherein said active-valve is controlled through a magnetic signal.

22. A vesicular shunt as recited in claim 12, further comprising a pump means for speeding the collection of fluid.

23. A vesicular shunt as recited in claim 12, further comprising a pump, wherein said pump is configured to transport fluid through the tube means for deposition in the bladder.

24. A vesicular shunt as recited in claim 12, wherein said tube means includes a valve located within said tube means.

25. A vesicular shunt as recited in claim 9, further comprising an anti-infective means.

26. A vesicular shunt as recited in claim 25, wherein said anti-infective means is a surface which encourages epithelialization.

27. A vesicular shunt as recited in claim 25, wherein said anti-infective means is a bactericidal material.

28. A vesicular shunt as recited in claim 25, wherein said anti-infective means is an entrained radioisotope.

29. A vesicular shunt as recited in claim 9, further comprising an anti-clogging means.

30. A vesicular shunt as recited in claim 29, wherein said anti-clogging means is an active ultrasound component.

31. A vesicular shunt as recited in claim 29, wherein said anti-clogging means is an inner and outer lumen.

32. A vesicular shunt as recited in claim 29, wherein said anti-clogging means is a surface which promotes epithelialization.

33. A vesicular shunt as recited in claim 29, wherein said anti-clogging means is an enzyme eluting material.

34. A vesicular shunt as recited in claim 9, further comprising a transport means for collecting fluid from remote interstices.

35. A method for draining excess fluid into the bladder of a living host, comprising:
- Implanting into the wall of the bladder a hollow cylinder, having an inside and an outside, and also having an inflow end and an outflow end;
- a valve, located inside said hollow cylinder, wherein said valve regulates the flow of fluid within the hollow cylinder such that fluid may flow from the inflow end of said hollow cylinder to the outflow end of said hollow cylinder;
- a flexible tube, having an inflow and an outflow end, the outflow end of said flexible tube being in fluid communication with the inflow end of said hollow cylinder;
- implanting the inflow end of the tube into the region to be drained, wherein the region to be drained is the pleural cavity.

36. The method of claim 35, wherein the host is a non-human mammal.

37. The method of claim 35, wherein the host is equine.

38. The method of claim 35, wherein the host is bovine.

39. The method of claim 35, wherein the host is feline.

40. The method of claim 35, wherein the host is canine.

41. The method of 35, wherein the host is a human.

* * * * *